(12) United States Patent
Kinnersley

(10) Patent No.: US 6,331,505 B1
(45) Date of Patent: *Dec. 18, 2001

(54) METHOD FOR INCREASING PLANT PRODUCTIVITY USING GLUTAMIC ACID AND GLYCOLIC ACID

(75) Inventor: Alan M. Kinnersley, East Lansing, MI (US)

(73) Assignee: Emerald BioAgriculture Corporation, Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/563,669

(22) Filed: May 2, 2000

Related U.S. Application Data

(63) Continuation-in-part of application No. 09/182,140, filed on Oct. 29, 1998, now Pat. No. 6,124,241.

(51) Int. Cl.$^7$ ............... A01N 37/36; A01N 37/44
(52) U.S. Cl. ............... 504/147; 514/547; 514/566
(58) Field of Search ............... 504/147; 514/547, 514/566

(56) References Cited

U.S. PATENT DOCUMENTS

| | | | |
|---|---|---|---|
| Re. 35,320 | 8/1996 | Kinnersley et al. | 504/161 |
| 3,679,392 | 7/1972 | Strauss et al. | 71/89 |
| 4,491,464 | 1/1985 | Ashmead et al. | 71/11 |
| 4,813,997 | 3/1989 | Kinnersley et al. | 71/66 |
| 4,908,353 | 3/1990 | Yamamoto et al. | 514/19 |
| 4,957,757 | 9/1990 | Law et al. | 426/281 |
| 5,439,873 | 8/1995 | Kinnersley | 504/158 |
| 5,593,947 | 1/1997 | Kinnersley et al. | 504/283 |
| 5,597,400 | 1/1997 | Nonomura et al. | 71/28 |
| 5,604,177 | 2/1997 | Kinnersley et al. | 504/147 |
| 5,814,582 | 9/1998 | Koskan et al. | 504/320 |
| 5,840,656 | 11/1998 | Kinnersley et al. | 504/115 |
| 5,972,840 | 10/1999 | Mottram | 504/244 |
| 6,008,256 | 12/1999 | Haraguchi et al. | 514/626 |

FOREIGN PATENT DOCUMENTS

| | | |
|---|---|---|
| 208 403 A1 | 1/1987 | (EP) . |
| WO 98/00012 | 1/1998 | (WO) . |

OTHER PUBLICATIONS

M. Santos, I. Claparols & J.M. Torne; "Effect of Exogenous Arginine, Ornithine, Methionine and GABA on Maize (Zea Mays L.) Embryogenesis and Polyamine Content,"J. Plant Physiol., vol. 142, 1993, pp. 74–80, XP002075993.

Derwent Publications Ltd., Class C03, AN 81–63554D, XP002075994 and JP 56032961B (Ajinomoto KK) (Abstract).

Chemical Abstracts 74:95454r (1971).

CABA Abstract 73:30077 (1973).

WPIDS Abstract 85–084635 (1985).

Chemical Abstract 93:235305n (1980).

Chemical Abstract 116:20002u (1991).

Chemical Abstract 99:36050z (1983).

SOLU–SPRAY Pamphlet by: Leffingwell Chemical Company, 1987.

"The Production and Efflux of 4–Aminobutyrate in Isolated Mesophyll Cells," Induk Chung, Alan W. Brown & Barry J. Shelp. Plant Physiol. 99:659–664, 1992.

"Comptes Rendus—Des Seances—De L'Academie Des Sciences; Physiologie Vegetale." C.R.Acad.Sc.Paris, t.271, Series D, pp2316–2319 (1970).

"Metabolism, Enzymology & Possible Roles of 4–Aminobutyrate in Higher Plants" (Review Article Number 51); V. Satya Narayan and P.M. Nair. Phytochemistry, 29:367–375, 1990.

"The Metabolism and Functions of γ–Aminobutyric Acid," Alan W. Brown and Barry J. Shelp. Plant Physiol. 115:1–5, 1997.

"Glycolate and glyoxylate stimulation of growth in Lemna gibba," Elisabeth Tillberg. Physiol.Plant 50:158–160, 1980.

"Effect of Low–Molecular–Weight Organic Acids of Peat Soil on the Growth of Barley Plants," V.I. Terent'ev, R.I. Tsareva, and O.V. Shchutskaya. Institute of Experimental Botany and Microbiology Belorussian Academy of Sciences; The Belorrusian Affiliate of the All–Union Botanic Society; Physiological and Biochemical Study of Plants. Minsk, 1965.

"On the Content of Organic Acids in Peat Soil and Their Effect on the Growth of Barley," Translated from Physiological Features of Cultivated Plants, Institute of Experimental Botany and Microbiology of the Academy of Sciences of the Byelorussian SSR, Byelorussian Division of the All–Union Botanical Society, Izd. Nauka I Tekhnika, Minsk, 1964.

"Nitrogen Metabolism in Plant Cell Suspension Cultures," Josef Behrend and Richard I. Mateles. Plant Physiol. 56:584–589, 1975.

Primary Examiner—S. Mark Clardy
(74) Attorney, Agent, or Firm—Woodard, Emhardt, Naughton, Moriarty & McNett

(57) ABSTRACT

Compositions including glutamic acid and either glycolic acid or polyglycolic acid, salts of these compounds or combinations thereof are described as are such compositions that include a calcium salt, preferably calcium nitrate. Methods of treating a plant including treating the plant or seed with a composition including glutamic acid and either glycolic acid or polyglycolic acid, salts of the aforementioned compounds or combinations thereof, and optionally a calcium salt, are also described. The methods and compositions of the present invention are advantageous in increasing plant productivity, including helping plants resist the effects of a wide variety of plant stresses. Methods of stimulating microbial growth with the compositions of the present invention are also provided.

53 Claims, 6 Drawing Sheets

METHOD FOR INCREASING PLANT PRODUCTIVITY USING GLUTAMIC ACID AND GLYCOLIC ACID

This application is a continuation-in-part of U.S. patent application Ser. No. 09/182,140, filed Oct. 29, 1998 now U.S. Pat. No. 6,124,241.

BACKGROUND OF THE INVENTION

The present invention relates generally to a process for increasing plant productivity. Specifically, the method relates to increasing plant productivity by treating roots, seeds, stems and/or foliage of plants with compositions containing glutamic acid and either polyglycolic acid or glycolic acid, and/or salts of the aforementioned compounds.

Many organic acids and amino acids, including glutamic acid and glycolic acid, are useful for stimulating plant growth. For example, in 1980, Tillberg (*Physiol Plant* 50:158–160) reported that duckweed growth was stimulated by 10 to 20% when low levels of glycolic acid (30–220 ppm) were added to culture media, although levels of 380 ppm or higher were inhibitory to growth. Oligomers of glycolic acid which are hydrolyzed to monomers have also been reported to stimulate duckweed growth (Kinnersley et al., U.S. Pat. No. 4,813,997). Behrend & Meteles (1975, *Plant Physiol.* 56:584–589) found that glutamic acid increased the growth of cell cultures of tobacco, tomato, and carrot, however, the effects of this amino acid on intact plants are less clear. Gorham (1950, *Canadian J. of Research* 28:356–381) found that glutamic acid (100 ppm) had negative effects on plant growth.

While increasing vegetative plant growth is important, of much greater significance is stimulation of reproductive growth that gives increased yield of fruits, vegetables, grains, etc. Compositions of organic acids that increase plant productivity, and in particular that increase reproductive growth, are therefore needed. The present invention addresses this need.

SUMMARY OF THE INVENTION

It has been discovered that a composition including glutamic acid, and either glycolic acid or polyglycolic acid, is effective in increasing plant productivity. Accordingly, in one aspect of the invention, a composition including a salt of glycolic acid and at least one of glutamic acid or a salt thereof is provided. In other forms of the invention, a composition may include glycolic acid and a salt of glutamic acid. In preferred forms of the invention, the salt of glycolic acid is an ammonium salt.

In another embodiment, a composition is provided that includes a salt of polyglycolic acid and at least one of glutamic acid or a salt thereof, wherein the polyglycolic acid has the following formula:

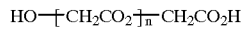

$$HO-[CH_2CO_2]_n-CH_2CO_2H$$

wherein n=1–10.

In other forms of the invention, compositions are provided that include polyglycolic acid and a salt of glutamic acid. In preferred forms of the invention, the salt of polyglycolic acid is an ammonium salt.

In further forms of the invention, the compositions described herein may further include a calcium salt to further increase plant productivity. In preferred embodiments, the calcium salt is calcium nitrate.

Other aspects of the invention provide methods of treating a plant which include treating a plant with the compositions described above. The methods are advantageous in increasing plant productivity, including increasing the growth of plants, increasing the ripeness of the fruit of plants and increasing the resistance of the plants to the effects of a wide variety of plant stresses, including environmental stresses.

Yet other aspects of the invention provide methods of stimulating microbial growth utilizing the compositions of the present invention.

It is an object of the invention to provide a composition with properties conducive for increasing plant productivity.

It is a further object of the invention to provide methods for treating a plant that increase plant productivity.

It is yet another object of the invention to provide methods for stimulating microbial growth.

Further objects and advantages of the present invention will be apparent from the following description.

DESCRIPTION OF THE PREFERRED EMBODIMENT

Figure 1:
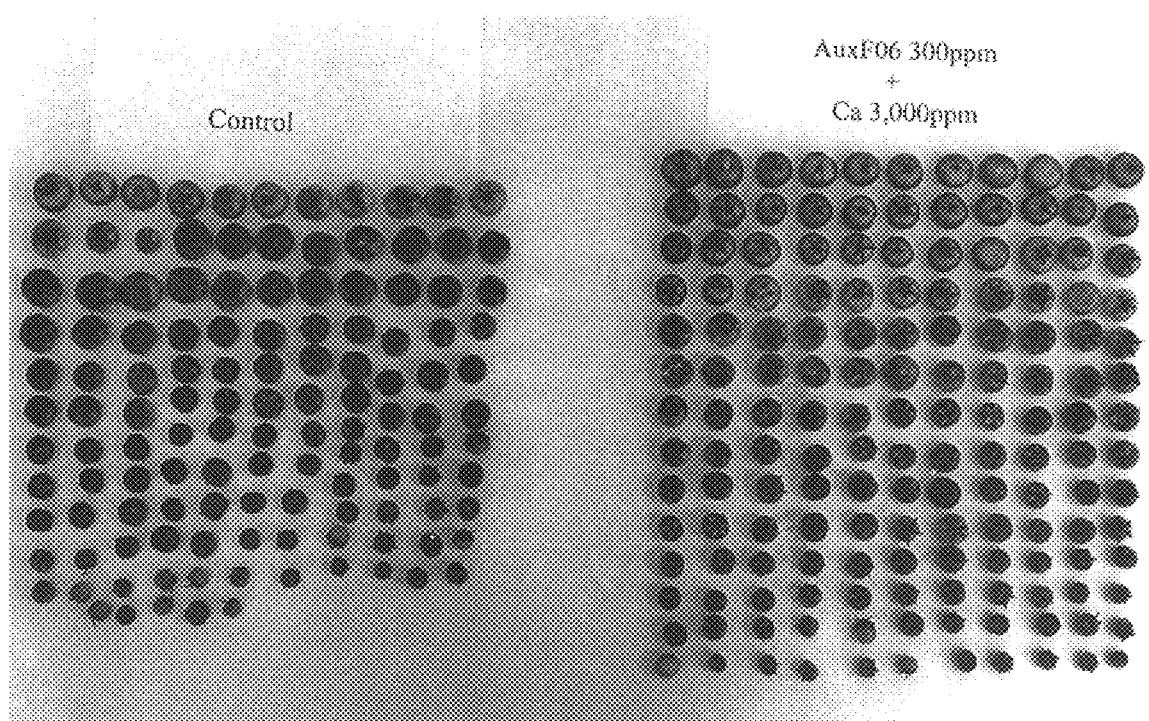
FIG. 1 depicts the effect of AuxF06 (a glutamic acid and glycolic acid composition) in combination with calcium nitrate on the yield of Tiny Tim tomatoes. Left panel: tomatoes from control plants; Right panel: tomatoes from plants treated with 300 ppm AuxF06 and 3000 ppm calcium nitrate.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to compositions comprising glutamic acid and either glycolic acid or polyglycolic acid. The polyglycolic acid has the following formula:

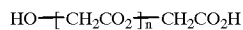

wherein n=1–10.

The compositions of the present invention have properties conducive for increasing plant productivity. For example, by combining glutamic acid and either glycolic acid or polyglycolic acid, an unexpected greater stimulation of plant growth occurs than is possible using either acid alone. The compositions are also very effective at increasing reproductive plant growth, increasing the ripening of fruit, the germination of seeds, and protecting plants from disease and other stresses. The compositions may thus allow for earlier harvesting of harvestable produce. optionally, calcium salts are included in the compositions to enhance the efficacy of the plant treatments. It has also unexpectedly been shown that an ammonium salt of glycolic acid is more effective than a similar amount of glycolic acid in increasing plant productivity and is therefore preferably included in the compositions described herein.

In a first aspect of the invention, a composition is provided that includes glutamic acid and glycolic acid.

Glutamic acid and glycolic acid may be obtained from commercial sources, may be synthesized by methods known in the art and may also be isolated from natural sources by methods known in the art. Any form of glycolic acid and glutamic acid may be used, including various salts. Illustrative carboxylate salts include salts formed from alkali metals, such as sodium and potassium, and ammonium salts, although others will also be useful. In a preferred form of the invention, the salt of glycolic acid is an ammonium salt, and may be made, for example, by neutralizing glycolic acid with ammonium hydroxide to a pH of 4.4. Thus, glycolic acid and/or a salt thereof may be combined with glutamic acid and/or a salt thereof to form various compositions of the present invention.

The concentrations of glutamic acid, glycolic acid and/or their salts in the compositions and the amount of the compositions effective in increasing plant productivity will depend on various factors, including the type of plant, the quantity of plants treated, and whether increased ripening, increased plant growth, or increased resistance to plant stress is desired. The desired concentrations and amounts can be determined by one skilled in the art. Typically, compositions include about 0.5 ppm to about 5,000 ppm [about 0.0067 oz/A to about 4.2 lbs/A] [about 0.47 g/ha to about 4.7 kg/ha] glycolic acid, and about 0.5 ppm to about 5,000 ppm [about 0.0067 oz/A to about 4.2 lbs/A] [about 0.47 g/ha to about 4.7 kg/ha] glutamic acid, but preferably include about 0.5 ppm to about 2,500 ppm [about 0.0067 oz/A to about 2.1 lbs/A] [about 0.47 g/ha to about 2.3 kg/ha] glycolic acid, and about 0.5 ppm to about 2,500 ppm . [about 0.0067 oz/A to about 2.1 lbs/A] [about 0.47 g/ha to about 2.3 kg/ha] glutamic acid, and more preferably, include about 50 ppm to about 500 ppm [about 0.67 oz/A to about 0.42 lbs/A] [about 46.7 g/ha to about 0.47 kg/ha] glycolic acid, and about 50 ppm to about 500 ppm [about 0.67 oz/A to about 0.42 lbs/A] [about 46.7 g/ha to about 0.47 kg/ha] glutamic acid. All amounts in ppm are on a weight/volume basis. Moreover, the application rates in brackets above are derived for a treatment utilizing a standard volume of 100 gallons of the specified solutions dispersed over 1 acre. It is further preferable that the compositions be comprised of a 1:1 composition of the components. A 1:1 composition as defined herein is a composition having equal weights of the individual components or equal volumes of solutions containing a single component provided the solutions are at the same concentration. The amounts above also apply to the salts of glutamic acid and glycolic acid.

In another form of the invention, the compositions above may further include a calcium salt. Any salt of calcium may be used, including chloride and sulphate. Calcium nitrate, however, is preferred. Addition of the calcium salt to a composition including glycolic acid and glutamic acid and/or their salts may further increase plant productivity. For example, addition of calcium nitrate to a composition comprising glutamic acid and glycolic acid increases reproductive plant growth and may increase the early ripening of harvestable produce, including fruit, to a greater extent than the same composition without calcium nitrate.

In compositions that include a calcium salt, such as calcium nitrate, the salt is typically present in amounts of about 100 ppm to about 10,000 ppm [about 0.083 lb/acre (lb/A) to about 8.3 lbs/A] [about 93 g/hectare (g/ha) to about 9.3 kg/ha], but may vary depending on the application.

In another forms of the invention, glutamic acid and/or a salt thereof may be combined with polymers of glycolic acid (polyglycolic acid) and/or a salt thereof to form a composition, where polyglycolic acid has the following formula:

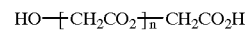

wherein n=1–10.

A composition may include glutamic acid and a 70% aqueous solution of glycolic acid which contains low levels of oligomers wherein n=2–4.

In a related embodiment, the compositions that include glutamic acid and polyglycolic acid, and/or their salts, may further include a calcium salt, preferably calcium nitrate, as discussed above for the compositions including glutamic acid and glycolic acid and/or their salts.

Polyglycolic acid may be produced by heating monomeric glycolic acid under reduced pressure at an elevated temperature as described in U.S. Pat. No. 4,813,997, which is hereby incorporated by reference. Linear condensation polymers of glycolic acid are most useful in the practice of the invention. The polymeric mixture obtained by heating monomeric glycolic acid under reduced pressure may be used without purification. However, the polymeric mixture can be separated into its components by various fractionation techniques known in the art, if desired. Moreover, small amounts of polymerized glycolic acid occur naturally in concentrated aqueous solutions of glycolic acid. The most cost effective source of glycolic acid is a 70% solution of glycolic acid, manufactured by DuPont, which contains 6–8% glycolic acid dimers. Similarly, methods for producing the various salts of polyglycolic acid are also well known in the art. To produce an ammonium salt of polyglycolic acid, for example, a solution of polyglycolic acid may be neutralized with ammonium hydroxide to a pH of 4.4.

The concentrations of glutamic acid and polyglycolic acid, and/or their salts, and the amount of the composition effective in increasing plant productivity will depend on the various factors as discussed above, but are typically the same as described above for glutamic acid and glycolic acid. Therefore, compositions typically include about 0.5 ppm to about 5,000 ppm [about 0.0067 oz/A to about 4.2 lbs/A] [about 0.47 g/ha to about 4.7 kg/ha] polyglycolic acid, and about 0.5 ppm to about 5,000 ppm [about 0.0067 oz/A to about 4.2 lbs/A] [about 0.47 g/ha to about 4.7 kg/ha] glutamic acid, but preferably include about 0.5 ppm to about 2,500 ppm [about 0.0067 oz/A to about 2.1 lbs/A] [about 0.47 g/ha to about 2.3 kg/ha] polyglycolic acid, and about 0.5 ppm to about 2,500 ppm [about 0.0067 oz/A to about 2.1 lbs/A] [about 0.47 g/ha to about 2.3 kg/ha] glutamic acid, and more preferably, include about 50 ppm to about 500 ppm [about 0.67 oz/A to about 0.42 lbs/A] [about 46.7 g/ha to about 0.47 kg/ha] polyglycolic acid, and about 50 ppm to about 500 ppm [about 0.67 oz/A to about 0.42 lbs/A] [about 46.7 g/ha to about 0.47 kg/ha] glutamic acid. It is further preferable that the compositions include a 1:1 composition of the components. In compositions that include a salt of nitric acid, such as calcium nitrate, the salt is typically present in amounts of about 100 ppm to about 10,000 ppm [about 0.083 lb/acre (lb/A) to about 8.3 lbs/A] [about 93 g/hectare (g/ha) to about 9.3 kg/ha], but may also vary depending on the application.

The compositions described herein may be combined with a carrier medium as known in the art. For example, the compositions may be combined with water, including tap water or with distilled water to which has been added selected minerals. The compositions may further be combined with an agricultural agent that may act as a carrier. For example, a fertilizer solution, pesticide solution, or herbicide solution may function as a carrier medium. The pesticide may be either a chemical or biological(natural) pesticide as known in the art, including fungicides, bacteriocides and anti-virals. The pesticides include antibiotics such as streptomycin and biological bacteriocides such as *Pseudomonas fluoroscens* commercialized as blight ban A506. One skilled in the art would be familiar with the various fertilizer, pesticide and herbicide solutions which may be employed. However, the compositions of the present invention are most simply combined with water.

The compositions may further include agricultural additives or formulation aids known to those skilled in the art. Such additives or aids may be used to ensure that the compositions disperse well in a spray tank, stick to or penetrate plant surfaces (particularly leaf or other foliage surfaces) as well as provide other benefits to the plant. For example, surfactants, dispersants, humectants, and binders may be used to disperse the compounds or compositions described herein in a spray tank as well as to allow the compounds or compositions to adhere to and/or penetrate the plant surfaces.

In yet another aspect of the invention, methods for treating a plant including treating the plant with the compositions described above are also provided. The compositions of the present invention are typically applied to the roots, stems, seeds and/or foliage of the plant. When the compositions are applied, such as in a foliar application, a hand sprayer may be used and the compositions may be sprayed to drip. The expression "sprayed to drip" is generally defined as a volume of about 100 gallons/acre (65 l/hectare). However, the compositions may also be applied hydroponically (as in Example 1), as a soil drench or as a seed coating.

The methods and compositions of the present invention may be used to increase a plant's reproductive as well as vegetative growth. The methods and compositions of the present invention may be used to treat recreational plants, decorative plants, trees or crops, and are particularly useful for treating commercial crops. Examples of plants and crops that may be treated in the present invention include monocotyledons, such as duckweed, corn and turf (including rye grass, Bermuda grass, blue grass, fescue), and dicotyledons, including crucifers (such as rape seed, radishes and cabbage) and solanaceae (including green peppers, potatoes and tomatoes).

The methods and compositions of the present invention may be used to increase the resistance of, and otherwise protect, a plant from the effects of a wide variety of plant stresses, including, for example, mechanical damage stress, nutrient stress, heat stress, cold stress, drought stress, water stress, salt stress and pathogen stress (including insect, bacterial, fungal and viral pathogen stresses). For example, treating plants with compositions including glutamic acid and either polyglycolic acid or glycolic acid, and/or salts of the aforementioned compounds, helps plants resist infection from diseases caused by, for example, fungi (including late blight, powdery mildew disease, Pythium, Rhizoctonia and Fusarium), bacteria (including Erwinia and Pseudomonas) and viruses (including tobacco mosaic virus and squash mosaic virus).

The methods and compositions of the present invention can further be used to stimulate seed germination as shown in Examples 11, 12 and 13. For example, the methods and compositions of the present invention may increase the rate of seed germination and/or may also increase the total number of seeds which germinate.

In yet another aspect of the invention, methods of treating microbes with at least one of glycolic acid or a salt thereof, and at least one of glutamic acid or a salt thereof, are provided. In further embodiments, a method includes treating the microbes with at least one of polyglycolic acid as described above or a salt thereof, and at least one of glutamic acid or a salt thereof. It has surprisingly been discovered that treating microbes with selected concentrations of such compositions increases, or otherwise stimulates, the growth of the microbes. In preferred forms of the invention, a microbe is treated with a composition including ammonium glycolate, or the ammonium salt of polyglycolic acid, and at least one of glutamic acid or a salt thereof. The microbes may be treated while cultured in a liquid medium, or the growth-stimulating compositions may be added to a solid nutrient medium upon which the microbes are grown.

The microbes are generally treated with an amount of the compositions that is effective in stimulating microbial growth. It must be realized that if microbes are treated with too large of an amount of, for example, polyglycolic acid or glycolic acid, microbial death may occur. Although the microbes may be treated with larger amounts depending on the situation, the microbes are generally treated with a composition that may include the above-recited amounts of glutamic acid, with typically no more than about 2,000 ppm glycolic acid or polyglycolic acid. The microbes are further preferably treated with a 1:1 composition, as defined above, of glutamic acid and at least one of glycolic and or polyglyolic acid. Other preferred compositions include about 1 ppm to about 1000 ppm of glutamic acid in combination with about 1 ppm to about 1000 ppm of at least one of glycolic acid or polyglycolic acid, and about 1 ppm to about 500 ppm glutamic acid in combination with about 1 ppm to about 500 ppm of at least one of glycolic acid or polyglycolic acid. These amounts also apply to the salts of glutamic acid, polyglycolic acid and glycolic acid. As compositions that include glutamic acid and the ammonium salt of either glycolic acid or polyglycolic acid are more effective than compositions that include glutamic acid and either glycolic acid or polyglycolic acid in stimulating microbial growth, less ammonium glycolate, or the ammonium salt of polyglycolic acid, compared to glycolic acid or polyglycolic acid, may generally be used. A wide variety of microbes may be treated, including bacteria and fungi.

Reference will now be made to specific examples using the methods and compositions described above. It is to be understood that the examples are provided to more completely describe preferred embodiments, and that no limitation to the scope of the invention is intended thereby.

EXAMPLE 1

Duckweed (*Lemna Minor* L) was grown following the general procedure described by Kinnersley (U.S. Pat. No. 5,439,873). Experiments were performed in which glycolic acid, polyglycolic acid, and glutamic acid were added to culture media separately and together and the effect on growth of duckweed was determined.

TABLE 1

| Treatments | Dry weight (mg) ± SD* | Increase in weight (mg) over control | Expected increase in weight (mg) over control |
|---|---|---|---|
| Control | 24.3 ± 4.7 | | |
| Glutamic Acid 500 ppm | 25.2 ± 2.8 | 1.1 | |
| Glycolic Acid 1000 ppm | 31.8 ± 2.8 | 7.5 | |
| Polyglycolic Acid 1000 ppm | 35.8 ± 6.4 | 11.5 | |
| Glutamic Acid 500 ppm + Glycolic Acid 1000 ppm | 40.3 ± 4.4 | 16.2 | 8.6 |
| Glutamic Acid 500 ppm + Polyglycolic Acid 1000 ppm | 62.4 ± 6.0 | 38.1 | 12.6 |

*Standard Deviation

The results in Table 1 show that the addition of 500 ppm glutamic acid increased dry weight (wt) of duckweed by 1.1 mg over control, and that polyglycolic acid (1000 ppm) increased dry weight by 11.5 mg. From this, the addition of 500 ppm glutamic acid and 1000 ppm polyglycolic acid together to the media should increase dry weight by 12.6 mg. The actual increase, 38.1 mg, was three times greater than the expected increase. By similar reasoning, it can be seen that mixtures of glycolic acid and glutamic acid increase plant growth more than expected from the activity of the acids alone.

EXAMPLE 2

A second duckweed experiment was performed in which the effect of polyglycolic acid was examined in combination with casein hydrolysate. The casein hydrolysate was an enzymatic digest (N-Z-amine) obtained from Sigma Chemical Company, (St. Louis, Mo.) which contained 18.58% glutamic acid. Results of this experiment are shown in Table 2.

The media used contained 5 g/L glucose in addition to the fertilizer that was used, as described in the previous example.

TABLE 2

| Treatments | Dry wt† (mg) ± SD† | Increase in weight (mg) over control | Expected increase in weight (mg) over control |
|---|---|---|---|
| Control | 44 ± 5 | | |
| Casein Hydrolysate 500 ppm | 58 ± 3 | 14 | |
| Polyglycolic Acid 500 ppm | 59 ± 12 | 15 | |
| Casein Hydrolysate 500 ppm + Polyglycolic Acid 500 ppm | 96 ± 15 | 52 | 29 |

†Standard Deviation

Results in Table 2 show that when casein hydrolysate was added to the medium, plant growth increased as shown by the 14 mg increase in weight of the plant. Addition of polyglycolic acid increased growth as shown by the 15 mg increase in weight of the plant. Addition of casein and polyglycolic together was thus expected to cause an increase in the weight of the plant by 29 mg (i.e., 15 mg+14 mg). However, the actual increase was 52 mg, a 79% greater than expected increase.

EXAMPLE 3

Tiny Tim tomatoes were grown in the greenhouse and treated with three foliar applications of mixtures of glutamic and glycolic acids with the first application being made at the first sign of fruit set. The second and third applications were made one week after the first application and the following week the ripe fruit from each plant was harvested. Results below show the average number of ripe fruit per plant, the average number of ripe fruit weighing more than 10 g per plant, and the total weight of ripe fruit harvested from each treatment. Each treatment and control had four replicates with three potted plants per replicate.

TABLE 3

| Treatment | # Fruit | DUN | % of Control | WT (g)* | DUN | % of NTC | Fruit Size** | DUN | % of NTC† |
|---|---|---|---|---|---|---|---|---|---|
| Non Treated Control (NTC) | 1.42 | a | 100 | 13.8 | a | 100 | 7.7 | a | 100 |
| GLU/GA 100 ppm | 4.5 | bcd | 317 | 50.6 | b | 368 | 11.2 | bc | 146 |

TABLE 3-continued

| Treatment | # Fruit | DUN | % of Control | WT (g)* | DUN | % of NTC | Fruit Size** | DUN | % of NTC[†] |
|---|---|---|---|---|---|---|---|---|---|
| GLU/GA 300 ppm | 4.4 | bcd | 311 | 52.5 | b | 381 | 12.4 | c | 161 |

*the total weight of ripe fruit from each treatment.
**average number of ripe fruit weighing more than 10 g.

Results in Table 3 show that mixtures of glutamic and glycolic acids [containing either 100 ppm GLU/GA (50 ppm GLU with 50 ppm GA) or 300 ppm GLU/GA (150 ppm GLU with 150 ppm GA)] increased the numbers and weight of ripe tomato fruit by more than three times when plants were given foliar applications of the acids. The numbers of large fruit were also increased in the treated plants. Duncans multiple range test (DUN) was used to analyze results for statistical significance, and all the increases were found to be statistically significant as indicated by the different letters following the treatments. A letter different from the control signifies a statistical difference at a probability of 95% or greater.

A second tomato experiment was performed using a lower amount of the glutamic/glycolic acid mixture and treating 7 week-old plants with only a single application, given at the onset of fruiting. One month after the treatment was given, all the fruit on the plants was removed and weighed and results are shown below in Table 4, results being expressed as a percentage of the control.

TABLE 4

| Treatment | % of Control for Extra-Large Fruit* | DUN[†] | % of Control for All Fruit | DUN[†] |
|---|---|---|---|---|
| Non-treated Control (NTC) | 100 | a | 100 | a |
| GLU/GA 50 ppm | 157 | a | 111 | a |
| GLU/GA 100 ppm | 147 | a | 123 | b |

*Fruit that weighs more than 10 g.
[†]DUN, Duncan's Multiple Range Test.

Results show that the glutamic acid (GLU)/glycolic acid (GA) composition at 100 ppm (i.e., 50 ppm GLU with 50 ppm GA) and 50 ppm GLU/GA, (i.e., 25 ppm GLU with 25 ppm GA) increased the amount of extra large tomatoes by about 150%. Total tomato productivity was significantly increased by 123% when plants were given 100 ppm of the acid mixture. The tomato experiments show that the present invention can be used to increase early ripening of tomatoes, to increase the average size of tomatoes, and to increase total tomato yield from plants.

EXAMPLE 4

Thai hot peppers (Park Seed, Greenwood, S.C.) were grown from seed and treated with mixtures of equal parts of glutamic acid (GLU) and glycolic acid either (GA) or polyglycolic acid (PGA). Foliar treatments were given three times at weekly intervals starting at the first sign of fruit formation when plants were six weeks old. Peppers were harvested one week following the third treatment and the average number of peppers and weight of peppers for each replicate was determined.

TABLE 5

| Treatment | #Peppers/Rep[‡] ± SD[†] | % Change from Control | FWT˙ (g) ± SD[†] | % Change from Control |
|---|---|---|---|---|
| Control | 15.3 ± 2.9 | 100 | 25.2 ± 3.3 | 100 |
| GLU/PGA 100 ppm | 16.7 ± 1.2 | 109 | 28.2 ± 8.9 | 112 |
| GLU/PGA 300 ppm | 16.3 ± 2.5 | 107 | 25.6 ± 7.3 | 102 |
| GLU/GA 100 ppm | 16.3 ± 2.1 | 107 | 31.3 ± 2.8 | 124* |
| GLU/GA 300 ppm | 18.0 ± 4.4 | 118 | 25.4 ± 3.7 | 101 |

*Significantly different from control at 0.90.
[†]Standard Deviation
˙Fresh weight
[‡]Rep, Repetition Results show that 1:1 mixtures of glutamic acid (GLU) and glycolic acid (GA) or polyglycolic acid (PGA) increased both the number of peppers and the total weight of peppers harvested per plant. The best responses were found at the lowest level of the mixtures.

EXAMPLE 5

The procedure followed in Example 3 was repeated but in this experiment lower levels of the mixed acids were used, and harvested peppers were separated according to size. Results are shown in Table 6.

TABLE 6

|  | Control | GLU + GA 50 ppm | % Change from Control |
|---|---|---|---|
| # Large Peppers | 4.0 ± 0.9 | 7.1 ± 0.8 | 139 |
| # Total Peppers | 8.2 ± 2.4 | 12.8 ± 1.8 | 156 |
| Wt. Large Peppers | 12.9 ± 2.4 | 15.9 ± 5.1 | 124 |
| Wt. Total Peppers | 14.1 ± 2.6 | 17.5 ± 4.8 | 124 |

The data in Table 6 shows the average values and respective standard deviation from three repetitions. Each replication consisted of three plants having similar amounts of flowering.

The results in Example 5 show that low levels of the bioactive mixture (less than 1 oz active ingredients/acre-71 g/hectare) significantly increased reproductive growth, as seen by the large increases in the average numbers of peppers/plant. The increased numbers of large and total peppers were significantly different at 0.99 and 0.90 respectively.

EXAMPLE 6

Seeds of Morris cabbage (Seedway, Elizabethtown, Pa.) were germinated in 5"×5" (12.7 cm×12.7 cm) green pots containing "Bacto" potting soil. Each treatment consisted of three repetitions and each repetition included two pots with ten plants/pot. After seven days, the cabbage seedlings were sprayed with a mixture of equal parts of glutamic acid (GLU) and glycolic acid (GA) equivalent to 1 oz/acre (73.1 ml/hectare) and 2 oz/acre (146.2 ml/hectare). Two additional applications were made at two and three weeks after seeding. Plants were harvested after four weeks and fresh weights determined. The results are shown below in Table 7.

TABLE 7

| Treatment | Average Fresh Weight (g) | % Change From Control |
|---|---|---|
| Untreated Control | 26.4 ± 1.2 | 100 |
| GLU + GA 150 ppm | 30.2 ± 1.7 | 114* |
| GLU + GA 300 ppm | 29.2 ± 2.8 | 111 |

*Significantly different (p > 0.95)

EXAMPLE 7

A second experiment was performed with a different variety of cabbage (Heads-Up cabbage, Harris Seeds, Rochester, N.Y.) that was grown following the procedure described in Example 6, except that the number of cabbage plants per pot was reduced to 6. In this second experiment, the effectiveness of the composition of this invention in promoting cabbage growth was compared using liquid or solid glycolic acid in mixtures with glutamic acid. The solid glycolic acid was Glypure™, a high purity crystalline source of glycolic acid from DuPont. The liquid glycolic acid was a 70% aqueous solution of glycolic acid containing about 6–8% diglycolic acid and small amounts of larger oligomers. The liquid glycolic acid was also obtained from DuPont.

Fresh and dry weights of cabbage plants treated with different formulations are shown below in Table 8. Results show that compositions containing both liquid and solid glycolic acid increase cabbage fresh and dry weights significantly compared to controls.

TABLE 8

| Treatments | Fresh wt avg Per 6 plants | % increase from control | Dry wt avg per 12 plants | % increase from control |
|---|---|---|---|---|
| Control | 28.2 ± 2.9 | 100 | 5.1 ± .7 | 100 |
| GLU/GA (solid)† 150 ppm | 32.2 ± .8* | 114 | 6.4 ± .2** | 125 |
| GLU/GA (solid)† 300 ppm | 33.4 ± 2.1 | 118 | 6.2 ± .8 | 122 |
| GLU/GA (liq.)†† 150 ppm | 33.2 ± 1.3 | 118 | 6.9 ± .4* | 124 |
| GLU/GA (liq.)†† 300 ppm | 34.0 ± 1.3** | 121 | 6.9 ± 3** | 135 |

*Significant at 90%
**Significant at 95%
†Solid form of glycolic acid (Glypure ™ from Dupont)
††Liquid form of glycolic acid (a 70% technical solution from DuPont)

EXAMPLE 8

A third tomato experiment was performed using Tiny Tim tomatoes grown in 4" (10.2 cm) black plastic pots. Each treatment included three replicates and each replicate included three plants. Plants were given two foliar treatments one week apart with the first treatment given when plants were seven weeks old. Plants were harvested one week after the second treatment and the number and weight of ripe and unripe fruit determined. Results are shown in Table 9. FIG. 1 shows the yield of fruit taken from a single replicate of treated and untreated plants. AuxF06 is the company designation for the mixture of glutamic and glycolic acids which is the subject of the invention.

TABLE 9

| Treatment | Average Weight (g) All Fruit ± SD* | Average Weight (g) of Ripe Fruit ± SD* |
|---|---|---|
| Untreated Control | 70.0 ± 5.35 | 8.2 ± 3.8 |
| GLU + GA 300 ppm | 85.5 ± 5.3 | 23.8 ± 4.8 |
| GLU + GA 300 ppm + CaNO$_3$ 3000 ppm | 92.9 ± 4.4 | 38.0 ± 3.1 |

*Standard Deviation

Results show that mixtures of equal parts of glycolic acid (GA) and glutamic acid (GLU) increased overall tomato productivity by 21% and increased productivity of ripe fruit by 290%. Addition of 3,000 ppm CaNO$_3$ to the mixed acids significantly increased the effects.

EXAMPLE 9

Lettuce plants were used to demonstrate the value of the present invention in protecting plants from disease. Waldmann/Grand Rapids green leaf, lettuce seed was sown ¼" (0.64 cm) to ½" (1.27 cm) deep in three 20" (50.8 cm) rows per flat. The flats measured 20"×10"×2" (50.8 cm×25.4 cm×5.1 cm) and were filled to the top with starter-fertilizer amended potting mix. After emergence, the seedlings were thinned to 25 plants per row (75 plants/flat). The overcrowding was intentional to increase Botrytis growth and infection. Four replicates were set up and the treatments were randomly organized. Plants were grown until nearly mature to gain row closure and sufficient senescent leaf debris for good saprophytic colonization after inoculation. The first test substance foliar treatment took place eight days prior to inoculation and the second treatment followed inoculation by eight days. Lettuce harvest occurred ten days following the second application.

Lettuce was treated with Benlate®, a fungicide, or with mixtures of glutamic acid and glycolic acid, that were given to plants as a foliar application or were left untreated. Eight days after the treatments, the lettuce was inoculated with Botrytis. Plants were given a second treatment eight days following infection and harvested ten days after the treatment. At harvest, plants were rated on a scale from 0 to 100 with 0 showing the least damage and 100 showing the most damage from fungal injection. Results of this rating are shown in Table 10.

TABLE 10

| Treatment | Disease Severity Rating |
|---|---|
| Non-Inoculated Control | 0 |
| Inoculated Control | 100 |
| Inoculated 1 oz. AuxF06 | 15 |
| Inoculated 2 oz. AuxF06 | 4 |
| Inoculated 16 oz. Benlate ® | 68 |
| Inoculated 4 oz. Benlate ® | 85 |

Figure 2:
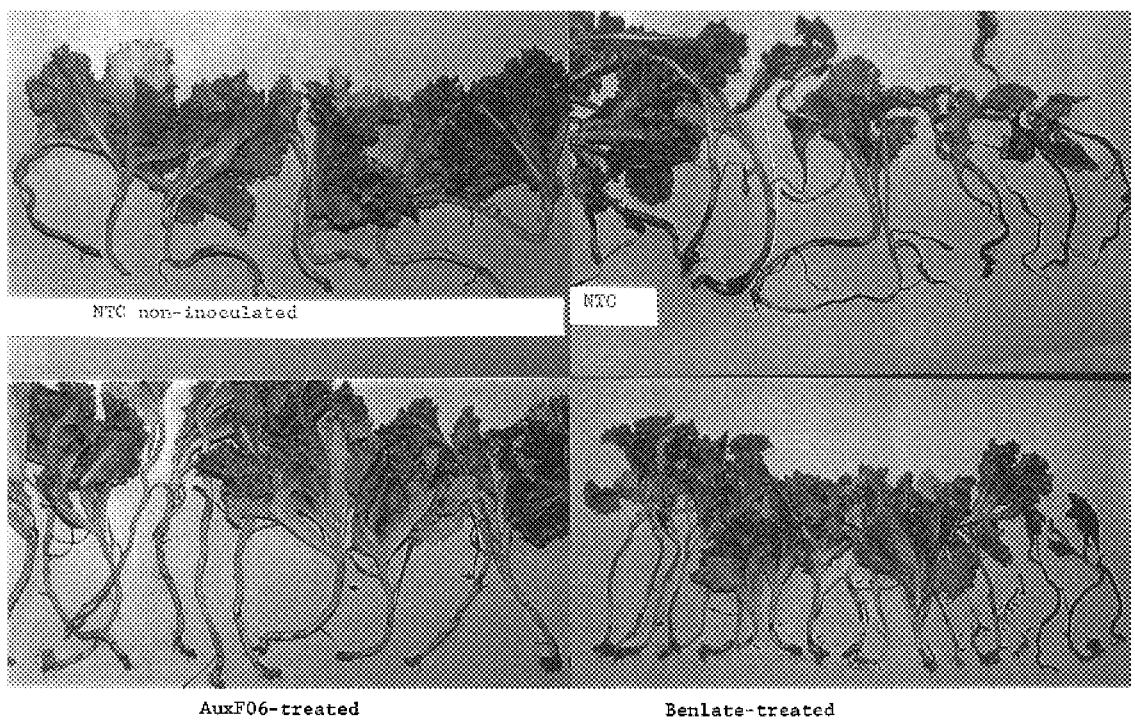
FIG. 2 depicts the effect of AuxF06 on resistance of lettuce plants to fungal infection. Top left panel: control non-inoculated cabbage plants; Top right panel: cabbage plants inoculated with Botrytis; Bottom left panel: cabbage plants treated with 2 oz/A (141 g/ha) AuxF06 and inoculated with Botrytis; Bottom right panel: cabbage plants treated with 16 oz/A (1.1 kg/ha) Benlate® and inoculated with Botrytis.

FIG. 2 shows representative plants from the treatments in Table 10. The discolored lesions on the stems of the infected plants indicate the severity of fungal infection. The non-treated control (NTC) that was not inoculated with Botrytis showed no signs of infection. Lettuce treated with the mixture of glutamic acid and glycolic acid (AuxF06) resisted infection much more successfully.

EXAMPLE 10

The value of the present invention in protecting plants from drought stress was investigated in a greenhouse experiment with Heads-Up Cabbage. Heads-Up cabbage seed (lot #79739-9c, 92% germ 9-97) was purchased from Harris Seeds Inc. and planted in 6×12 well plug flats. Seedlings were transplanted at the one-true-leaf stage into half-gallon pots at 2 per pot. Plants received the first spray treatment at approximately 2.5 mL per plant when they had reached an average of 7 true-leaves per plant. The second treatment was applied 5 days later, just following the final watering of the plants to be drought treated. The soil moisture content was measured at drought initiation. A plotting of the soil moisture points gave a nearly perfect "Normal" distribution pattern. The drought treatment was performed by withholding water until a severe wilt was apparent, but without passing the permanent wilting point. At 7 days following drought initiation, pots were watered, terminating the drought treatment. At 24 hr following drought termination the plants were harvested. Fresh and dry weights of all plants were measured.

Figure 3:
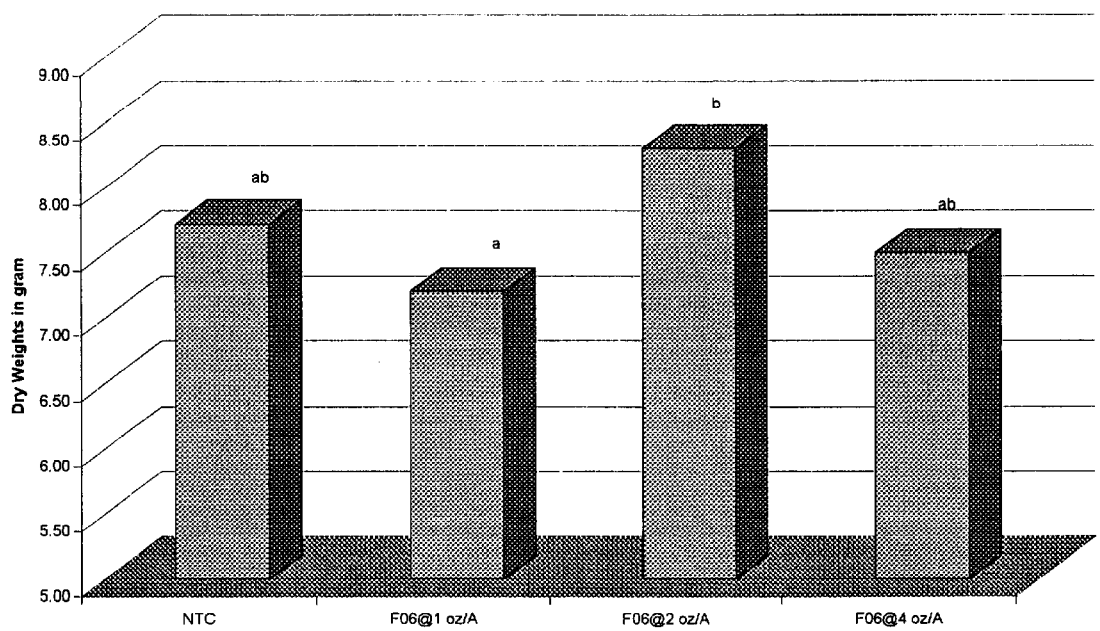
FIG. 3 depicts a bar graph showing the dry weight of cabbage plants after being treated with AuxF06. The top panel represents cabbage plants that were well watered (i.e., not subject to drought conditions) and the bottom panel represents cabbage plants that were drought-stressed and subsequently rehydrated. The bars in each panel, from left to right, represent a non-treated control, treatment with AuxF06 at 1 oz/A (71 g/ha), treatment with AuxF06 at 2 oz/A (141 g/ha) and treatment with AuxF06 at 4 oz/A (282 g/ha).
Figure 3:
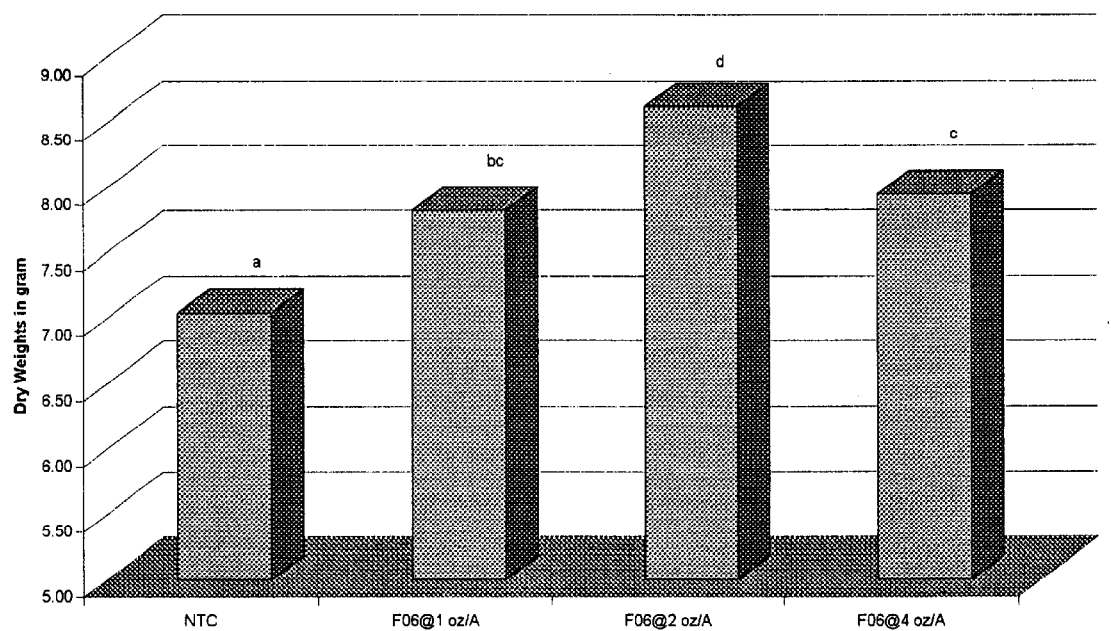

The results are shown in the bar graph in FIG. 3. As a result of the drought treatment, non-treated control plants weighed an average 7.0 g or about 10% less than the average weight of well-watered plants not subjected to the drought treatment, which weighed an average 7.8 g. In spite of the drought treatment, the cabbage plants treated with the composition of the invention (designated "F06" in the figure) had increased in weight. The letters above each bar on the graph denotes statistical significance. Statistical analysis of the results shows that, although the most effective rate of F06 (2 oz/A) (141 g/hectare) increased cabbage weight of well watered plants by 6.4% the difference was not significant. When plants were drought stressed the comparable increase in weight was 2.9% and highly significant. Plants treated with F06 at 1 oz/A (71 g/ha) and 4 oz/A (282 g/ha) were also significantly heavier than controls following drought stress. These results demonstrate the effectiveness of the present invention in preventing loss of agricultural yields due to drought stress.

EXAMPLE 11

The effect of the composition of this invention on seed germination was studied in a petri dish experiment. A single Whatman (Maidstone, UK) 90 mm filter paper was placed in each petri dish and 5 ml of treatment solution were added to the dish. 130 seeds of Kentucky Blue Grass were then added to each dish. After 6 days, the number of seeds germinated in each petri dish was counted and results shown below in Table 11.

TABLE 11

| Treatments | # germinated Seeds, avg. per petri dish | % increase from control |
|---|---|---|
| Control | 12.3 ± 2.5 | 100 |
| GLU/GA 100 ppm | 32.0 ± 2.4 | 260 |
| GLU/GA 10 ppm | 16.0 ± 2.2 | 130 |
| GLU/GA 1 ppm | 14.7 ± 2.1 | 120 |
| GLU/GA 0.1 ppm | 15.7 + 1.2 | 127 |

This example relates to a Kentucky Blue Grass seed germination study performed in petri dishes. Results show that the treatment containing 100 ppm w/v of the glutamic/glycolic acid solution increased germination 260% over controls. The glycolic acid used in this experiment was crystalline Glypure™ from DuPont.

EXAMPLE 12

Figure 4:
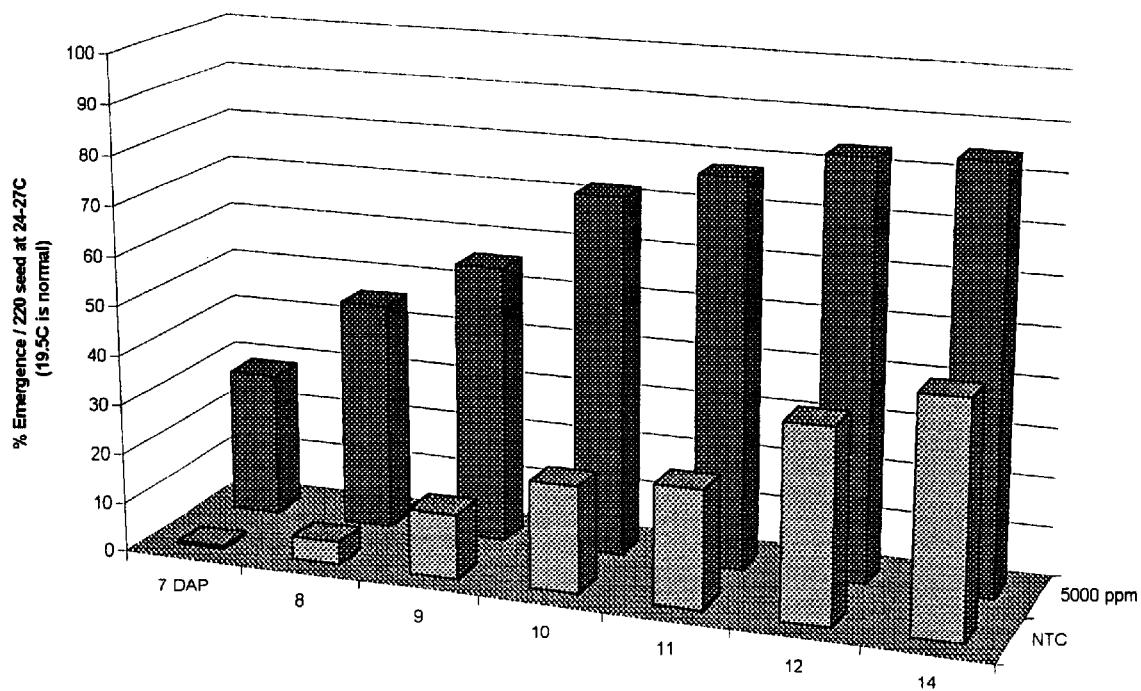
FIG. 4 depicts a bar graph showing the percentage of germinated petunia seeds coated with AuxF06 as a function of the number of days after planting (DAP). Bars in the foreground represent non-treated controls (NTC) whereas bars in the background represent germinated petunias after being treated with 5,000 ppm AuxF06.

The glutamic acid/glycolic acid composition used in the previous example was mixed with polyvinyl-pyrrolidone (Sigma Chemicals, St. Louis, Mo.) to form a mixture that was used to coat seeds. Seeds are often commercially coated with pesticides and other agents to increase the viability of germinated seedlings. In this experiment, a coating solution was made from a solution containing 5,000 ppm w/v glutamic acid/glycolic acid with 24 g polyvinyl-pyrrolidone. The mixture was used to coat petunia seeds (Ultra Red Star, Goldsmith Seed, Gilray, Calif.) in the manner described below: Approximately 1000 petunia seeds were placed in a small dish and 2–3 ml of the coating solution was poured over the seeds. Seeds were agitated with the mixture until all were coated (2–4 minutes). The seed suspension was then poured onto an absorbent surface to remove the excess fluid. After a few minutes, seeds were removed and air-dried. The dried seeds and non-coated control seeds were planted in a seedling planting mix and the number of germinated seedlings counted at different days after planting (DAP). Results are shown below in the bar graph (FIG. 4). AuxF06 is the company designation of the glutamic acid/glycolic acid mixture. The results show that seeds coated with the composition of this invention germinated much faster than control seeds. A week after seeds had been planted, none of the untreated seeds had germinated whereas, at this time, over 35% of the treated seeds had germinated. Two weeks after planting, more than twice as many of the coated seeds had germinated than had controls.

EXAMPLE 13

A cotton seed sample (Fibermax 832) was received from a Georgia cotton farmer which was fungicide coated (blue). A coating solution was created from 200 ml F06 at 5000 ppm with 24 g polyvinyl-pyrrolidone (molecular weight= 10,000, PVP-10). Approximately 200 cotton seeds were poured into a small weighboat. Coating solution was poured over the seeds to submersion. The solution was mixed until all seed was wetted (2–4 min). The coating solution was then poured off and the seed spread out onto an absorbent surface and allowed to dry. The control was only treated with the fungicide, not F06.

The following day ($\geq$12 hr later) control and coated seed was planted 1 inch subsurface in seedling planting mix. Placement was 1 seed/well in 6×12 well flats. Results are shown in FIG. 5.

Figure 5:
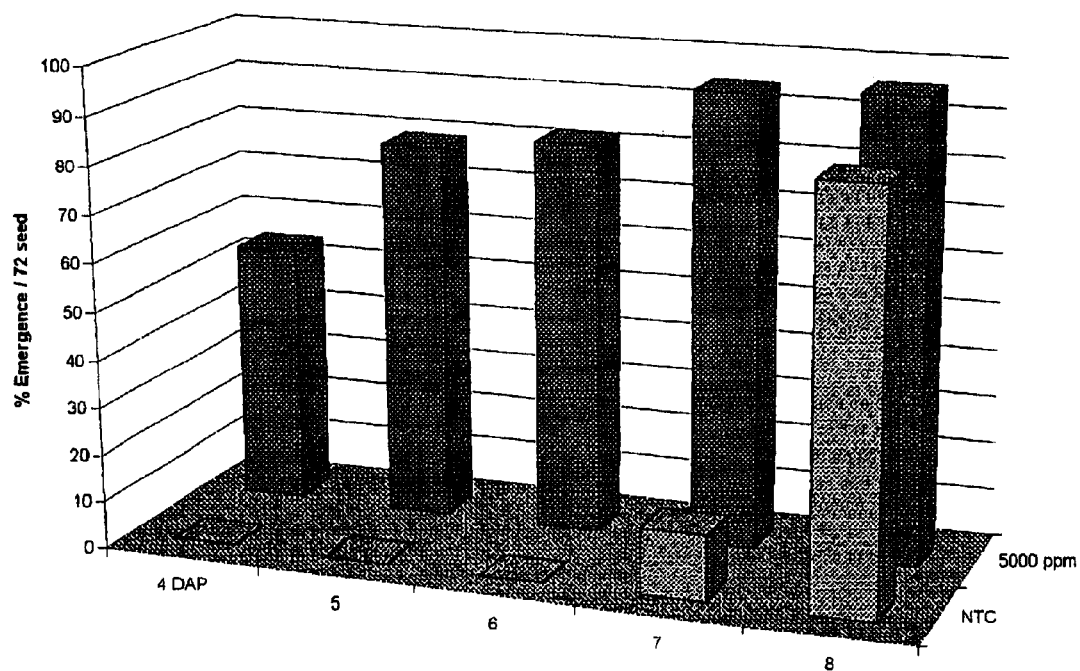
FIG. 5 depicts a bar graph showing the percentage of germinated cotton seeds coated with an AuxF06/polyvinyl pyrrolidone solution as a function of the number of days after planting. Bars in the foreground represent non-treated controls (NTC) whereas bars in the background represent seeds treated with 5,000 ppm AuxF06.

FIG. 5 shows that seeds coated with AuxF06 in combination with the fungicide polyvinyl-pyrrolidone germinated faster than control seeds. A week after seed had been planted, only about 10% of the non-treated control seed had germinated, whereas over 90% of the treated seeds had germinated.

EXAMPLE 14

Red Robin tomato seed (Park Seed, Greenwood, S.C.) was planted in plug trays, one seed per plug and lightly covered with soil. Seedlings were transplanted when they had reached the 3–4 twice leaf stage, about 2–3 weeks after planting. Seedlings were transplanted into 4.0" pots and three potted seedlings were placed into 1 Perma-Nest tray. Each repetition (rep) consisted of three trays, and each treatment had 3 repetitions. A treatment application of a composition including 75 ppm ammonium glycolate and 75 ppm glutamic acid was given at the time indicated in the table below. Plants were fertilized every two weeks starting 3–4 days after the first treatment application. Fertilization was provided by giving each pot 100 ml. of a 20-20-20 NPK tablespoon of fertilizer in 1 gallon of water. Tomato fruit was harvested 12 weeks after planting.

Results below show the total number and weight of all tomatoes (i.e., ripe and unripe tomatoes) and ripe tomatoes harvested 12 weeks after planting.

TABLE 12

| Time of Treatment | # Ripe Fruit | Weight Ripe Fruit (g) | Total # of all Fruit | Total Weight of all Fruit (g) | % Change |
|---|---|---|---|---|---|
| Control | 16 ± 7 | 129.7 ± 46 | 29 ± 3 | 191.6 ± 26 | 100 |
| F25 First Bud | 27 ± 7 | 203.8 ± 73 | 32 ± 11 | 222 ± 76 | 116 |
| F25 Full Flowering | 32 ± 6 | 228.3 ± 28 | 45 ± 7 | 267 ± 32 | 140 |
| F25 Fruit Set | 29 ± 8 | 210.7 ± 51 | 42 ± 8 | 260 ± 40 | 136 |

Results show that when an equal weight mixture of ammonium glycolate and glutamic acid was given to plants at full flowering, total weight of tomatoes was increased by 40%.

Statistical analysis showed that the increase in number and weight of tomatoes from treating plants with 75 ppm F25 at full flowering was significant ($p \geq 0.95$).

EXAMPLE 15

The bioactivity of mixtures of glutamic acid and glycolic acid and mixtures of glutamic acid and the ammonium salt of glycolic acid were compared by observing microbial growth of *Sclerotinia minor*. Potato dextrose agar (PDA), obtained from Becton Dickinson Microbiolgy Systems (Sparks, Md.), was poured into sterile disposable petri dishes (100 mm×15 mm) and inoculated with Sclerotinia minor sclerotia to start new cultures on day zero. The cultures had reached an appropriate stage of maturation for use in the test after two weeks of growth. Mutliple 1 L containers of PDA were prepared and autoclaved on day 14. The containers remained in the circulating water bath at 46° C. until the solutions were read for adddition (about 2 hours). Mixtures of glutamic acid and glycolic acid (F06) and mixtures of glutamic acid and the ammonium salt of glycolic acid (F25) were added to the 46° C. PDA through a syringe-tip 0.2 $\mu$m-pore sterile filtration disc in a positive laminar-flow sterile hood and thoroughly mixed before returning to the 46° C. water bath to await pouring. Stacks of 22 dishes were poured for each medium type and allowed to solidify and cool overnight.

Soft, white to gray, sclerotial clumps of hyphae wer picked form the culture dishes on day 15 with heat-sterilized forceps and transferred and one clump was transferred to the center of each test medium dish. Twenty dishes of each inoculated medium were stacked and replaced into the plastic sleeves they were originally packaged in for incubation at room temperature (about 23° C.). Some of the cultures had just reached the edges of the medium after 4 days of growth. The radius of each colony was measured.

Figure 6:
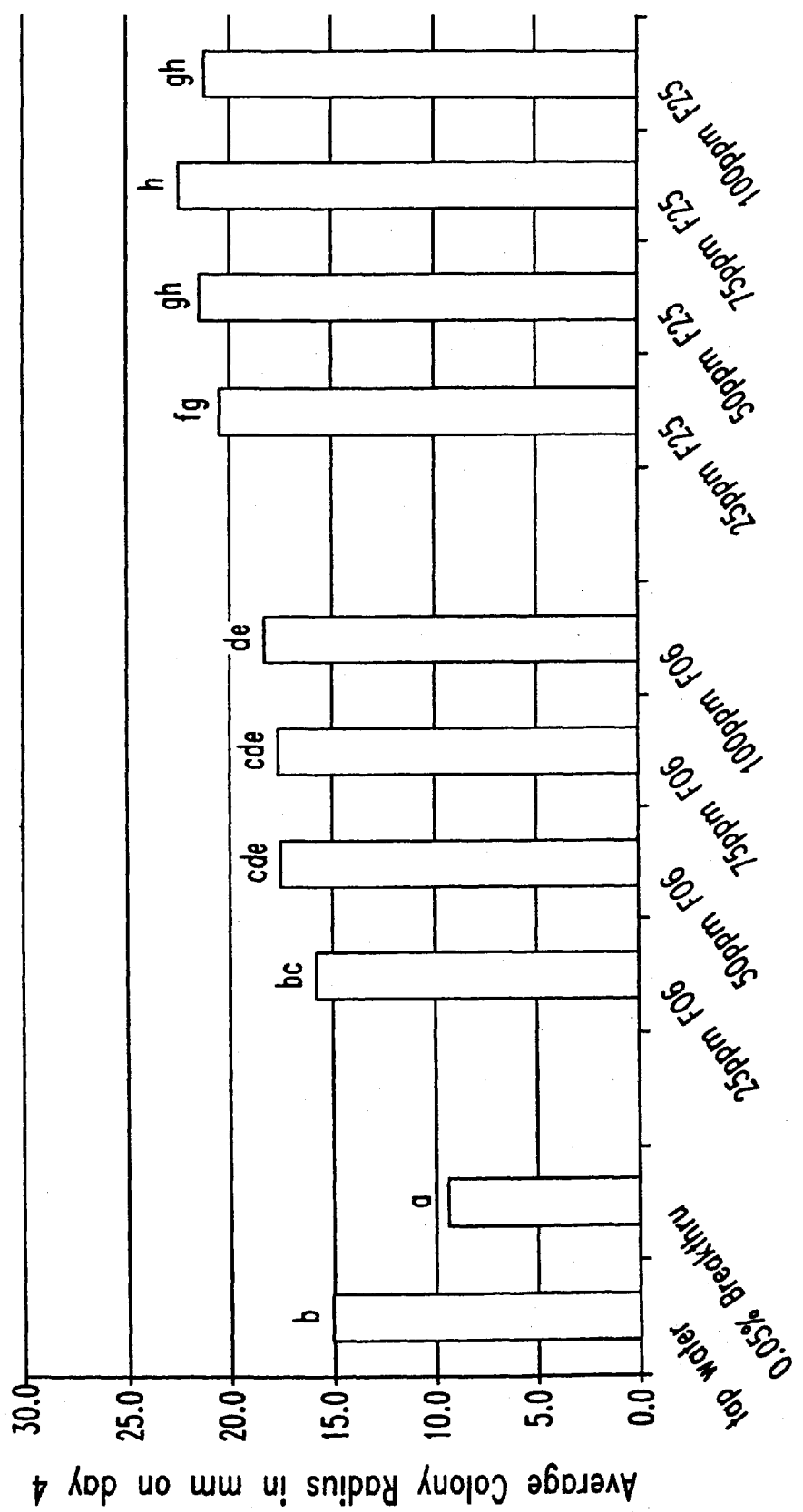
FIG. 6 depicts a bar graph showing the effects of compositions including glutamic acid and glycolic acid (F06) and compositions including glutamic acid and ammonium glycolate (F25) on growth of *Sclerotinia minor*. Colonies of *Sclerotinia minor* were treated with the indicated concentrations (in ppm, on a weight/volume basis) of F06 and F25 as more fully described in example 15. Breakthru®, a silicone-based surfactant; the lower case letters above the bars represent Duncan groupings, which indicate significant differences between any two groups when no letters are shared between the groups.

As shown in FIG. 6, F25 was signficantly more effective at promoting microbial growth than F06 as determined by Duncan multiple comparison analyses for observed means at a confidence interval of 95% (i.e., $p \geq 0.95$).

While the invention has been illustrated and described in detail in the forgoing description, the same is to be considered as illustrative and not restrictive in character, it being understood that only the preferred embodiments have been shown and described, and that all changes and modifications that come within the spirit of the invention are desired to be protected. In addition, all references cited herein are indicative of the level of skill in the art and are hereby incorporated by reference in their entirety.

What is claimed is:

1. A composition, comprising a salt of glycolic acid and at least one of glutamic acid or a salt thereof.

2. The composition of claim 1, wherein said glutamic acid and said salt of glycolic acid are present in amounts effective in increasing plant productivity.

3. The composition of claim 1, wherein salt of glycolic acid is an ammonium salt.

4. The composition of claim 1, wherein said composition is in a carrier medium.

5. The composition of claim 4, wherein said carrier medium is an agricultural agent.

6. The composition of claim 5, wherein said agricultural agent is selected from the group consisting of fertilizers, herbicides and pesticides.

7. The composition of claim 4, wherein said carrier medium is water.

8. The composition of claim 1, said composition further comprising a calcium salt.

9. The composition of claim 8, wherein said calcium salt is calcium nitrate.

10. The composition of claim 1, wherein said composition comprises about 0.5 ppm to about 2,500 ppm glutamic acid, and about 0.5 ppm to about 2,500 ppm of a salt of glycolic acid, all on a weight/volume basis.

11. A composition, comprising glycolic acid and a salt of glutamic acid.

12. A composition, comprising a salt of a polyglycolic acid and at least one of glutamic acid or a salt thereof, said polyglycolic acid having the following formula:

$$HO-[CH_2CO_2]_n-CH_2CO_2H$$

wherein n=1–10.

13. The composition of claim 12, wherein said composition comprises about 0.5 ppm to about 2500 ppm glutamic acid, and about 0.5 ppm to about 2,500 ppm of a salt of polyglycolic acid, all on a weight/volume basis.

14. The composition of claim 12, wherein said salt of polyglycolic acid is an ammonium salt.

15. The composition of claim 12, wherein said composition is in a carrier medium.

16. The composition of claim 15, wherein said carrier medium is water.

17. The composition of claim 15, wherein said carrier medium is an agricultural agent.

18. The composition of claim 12, said composition further comprising a calcium salt.

19. The composition of claim 18, wherein said calcium salt is calcium nitrate.

20. A composition, comprising a polyglycolic acid and a salt of glutamic acid, said polyglycolic acid having the following formula:

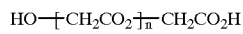

wherein n=1–10.

21. A method of treating a plant, comprising treating the plant with a composition comprising a salt of glycolic acid and at least one of glutamic acid or a salt thereof.

22. The method of claim 21, wherein said composition comprises about 0.5 ppm to about 2,500 ppm glutamic acid and about 0.5 ppm to about 2,500 ppm of a salt of glycolic acid, all on a weight/volume basis.

23. The method of claim 21, wherein said salt of glycolic acid is an ammonium salt.

24. The method of claim 21, wherein said composition is in a carrier medium.

25. The method of claim 24, wherein said carrier medium is water.

26. The method of claim 24, wherein said carrier medium is an agricultural agent.

27. The method of claim 26, wherein said agricultural agent is selected from the group consisting of fertilizers, herbicides and pesticides.

28. The method of claim 21, wherein the composition further comprises a calcium salt.

29. The method of claim 28, wherein said calcium salt is calcium nitrate.

30. The method of claim 29, wherein said composition comprises about 0.5 ppm to about 2,500 ppm glutamic acid, about 0.5 ppm to about 2,500 ppm glycolic acid and about 100 ppm to about 10,000 ppm calcium nitrate.

31. The method of claim 21, which further comprises treating the plant with an amount of the composition effective to increase plant productivity.

32. The method of claim 21, wherein said plant yields harvestable produce.

33. The method of claim 21, wherein said composition is applied to the plant in amounts effective to increase early ripening of the produce.

34. The method of claim 21, wherein said composition is applied to the plant in amounts effective to increase the growth of said plant.

35. The method of claim 21, wherein said composition is applied to the plant in the amounts effective to increase plant resistance to plant stresses.

36. The method of claim 35, wherein said plant stress is drought stress.

37. The method of claim 35, wherein plant stress is pathogen stress.

38. The method of claim 21, wherein said composition is applied to seeds of said plant in amounts effective to stimulate seed germination.

39. A method of treating a plant, comprising treating the plant with a composition comprising glycolic acid and a salt of glutamic acid.

40. A method of treating a plant, comprising treating the plant with a composition comprising a salt of a polyglycolic acid and at least one of glutamic acid or a salt thereof, said polyglycolic acid having the following formula:

wherein n=1–10.

41. The method of claim 40, said composition further comprising a calcium salt.

42. The method of claim 41, wherein said calcium salt is calcium nitrate.

43. The method of claim 42, wherein said composition further comprises about 100 ppm to about 10,000 ppm of said calcium nitrate.

44. The method of claim 40, wherein said salt of polyglycolic acid is an ammonium salt.

45. The method of claim 40, wherein said composition is in a carrier medium.

46. The method of claim 40, which further comprises treating the plant with an amount of the composition effective to increase plant productivity.

47. The method of claim 40, wherein said composition comprises about 0.5 ppm to about 2,500 ppm glutamic acid and about 0.5 ppm to about 2,500 ppm of a salt of polyglycolic acid.

48. The method of claim 40, wherein said composition is applied to seeds of said plant in amounts effective to stimulate seed germination.

49. A method of treating a plant, comprising treating the plant with a composition comprising polyglycolic acid and a salt of glutamic acid, said polyglycolic acid having the following formula:

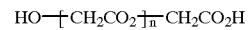

wherein n=1–10.

50. A method of increasing microbial growth, comprising treating the microbe with an effective, amount of at least one of glutamic acid or a salt thereof, and at least one of glycolic acid or a salt thereof.

51. The method of claim 50, wherein the salt of glycolic acid is an ammonium salt.

52. A method of increasing microbial growth, comprising treating the microbe with an effective amount of at least one of glutamic acid or a salt thereof, and at least one of polyglycolic acid or a salt thereof, said polyglycolic acid having the following formula:

wherein n=1–10.

53. The method of claim 52, wherein said salt of polyglycolic acid is an ammonium salt.

* * * * *